United States Patent [19]

Wilson

[11] 4,149,280
[45] Apr. 17, 1979

[54] STRUCTURE OF A STABILIZED ARTIFICIAL LIMB

[76] Inventor: Michael T. Wilson, 1259 Monument Blvd., Concord, Calif. 94520

[21] Appl. No.: 805,058

[22] Filed: Jun. 9, 1977

[51] Int. Cl.² ............................................. A61F 1/04
[52] U.S. Cl. .............................................. 3/22; 3/30
[58] Field of Search ...................... 3/21, 22, 12, 26, 2, 3/30–32; 287/12, 21

[56] References Cited

U.S. PATENT DOCUMENTS

| 3,414,908 | 12/1968 | Waggott et al. | 3/21 X |
| 3,790,965 | 2/1974 | Gelbenegger | 3/22 X |
| 3,906,552 | 9/1975 | Weber | 3/21 X |
| 3,982,278 | 9/1976 | May | 3/21 |

FOREIGN PATENT DOCUMENTS

| 2101254 | 7/1972 | Fed. Rep. of Germany | 3/21 |
| 2217261 | 3/1973 | Fed. Rep. of Germany | 3/21 |
| 214096 | 4/1924 | United Kingdom | 3/21 |
| 978586 | 12/1964 | United Kingdom | 3/21 |

Primary Examiner—E. H. Eickholt
Attorney, Agent, or Firm—Phillips, Moore, Weissenberger, Lempio & Majestic

[57] ABSTRACT

The structure for an artificial limb includes a domed element and a hollow cylindrical coupling defining a beveled outer surface at one end thereof. The hollow cylindrical coupling is positionable within the beveled outer surface adjacent the domed element to form a bondable joint therebetween.

11 Claims, 8 Drawing Figures

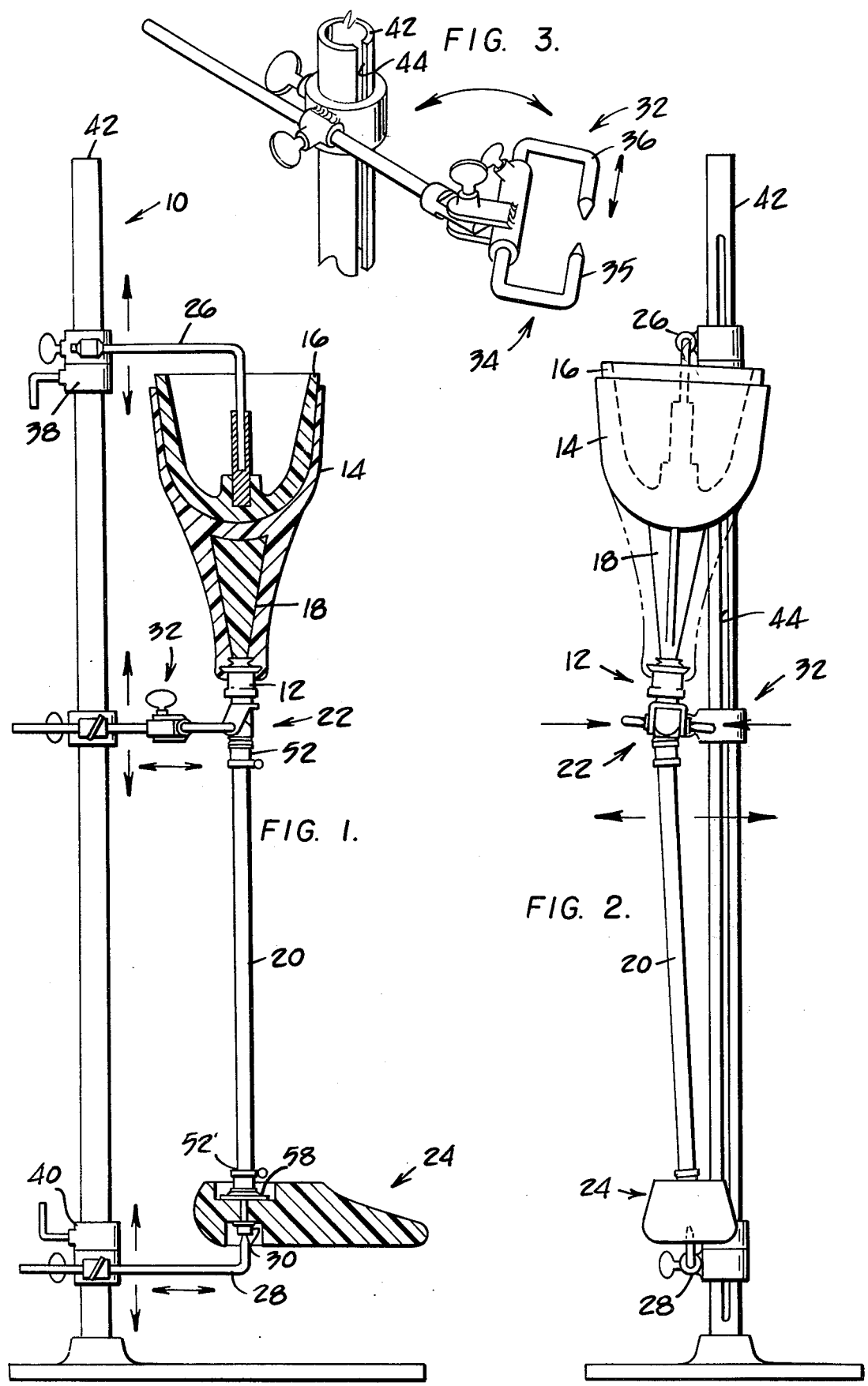

FIG. 7.
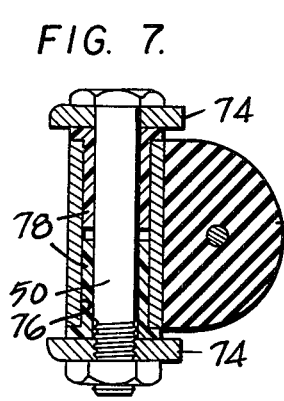
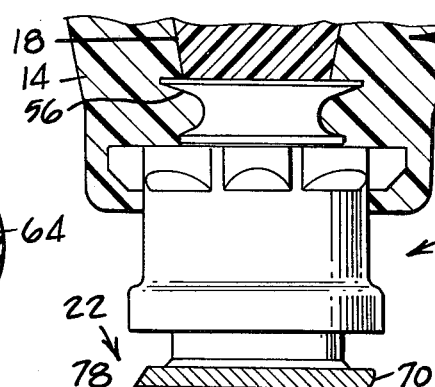
FIG. 5.
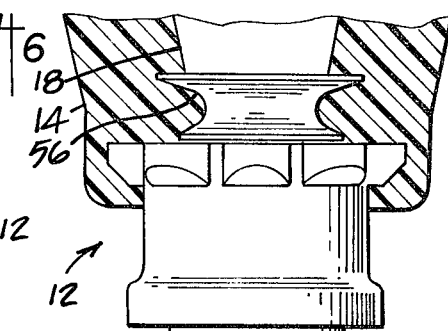
FIG. 6.
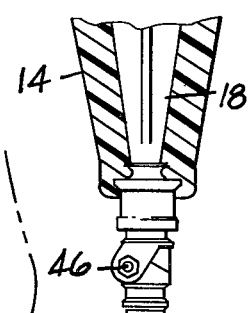
FIG. 4.
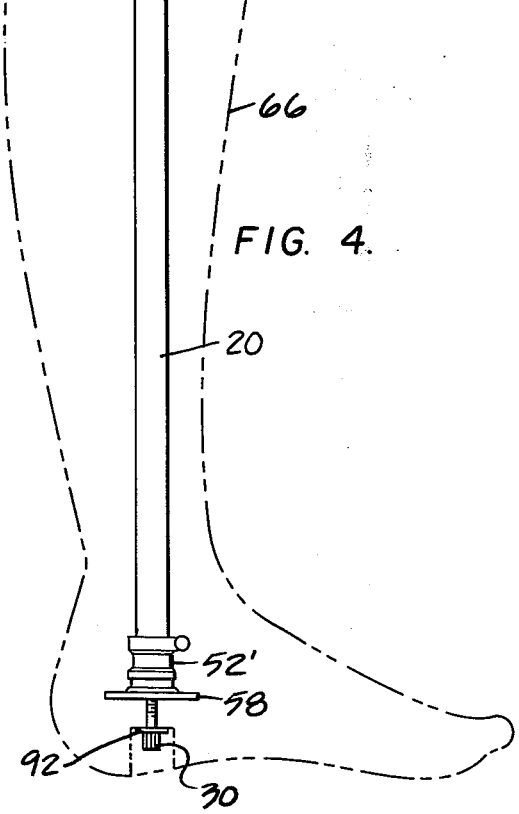
FIG. 8.
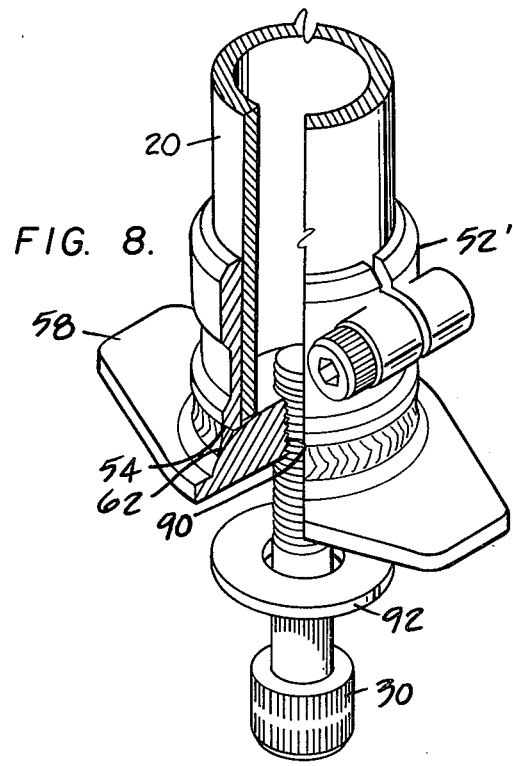

STRUCTURE OF A STABILIZED ARTIFICIAL LIMB

BACKGROUND OF THE INVENTION

This invention relates to the stabilization of artificial limbs.

Artificial limbs are generally fitted to patients by a skilled prosthetist utilizing components available in the art to make up the artificial limb. Until recently, artificial limbs were generally of the exoskeletal type, and where the artificial limb was to replace a leg removed above the knee, a complex knee joint was incorporated into the exoskeletal device, usually having some sort of a brake or release mechanism to allow flexing of the knee.

In recent years, the endoskeletal prosthetic device has been developed for use in replacing lower limbs, both in below-the-knee and above-the-knee amputations. An endoskeletal device more closely approximates the human structure in that the strength member usually includes a tubular structure approximating a human bone. By concentrating the strength member into a tubular skeletal-type prosthetic device considerable weight can be saved. Nevertheless, the uniqueness of each prosthetic device still requires individual fitting to the patient. Knee joints and bases to mount a prosthetic foot are currently available for use in such fitting. These devices incorporate adjustment features so that the individual prosthetic device may be fitted to the particular needs of the patient.

Although these adjustable prosthetic devices have proved very useful, they suffer from several drawbacks. First, adjustable fittings loosen after wear and must be reset to the measurements of the patient. Secondly, the adjustable elements may increase the weight of the entire prosthetic device, which is immediately reflected in patient fatigue. Furthermore, the increase in weight of a relatively long prosthetic device necessary in an amputation above the knee imposes a relatively large moment on the patient's relatively short stump. Accordingly, it is appropriate to reduce weight to a minimum in any prosthetic device without loss of strength.

Nevertheless, since each device must be uniquely tailored to the patient, the use of adjustable fittings for the attachment of pylons, the knee joint, and also what suffices to be an ankle joint, has become common. Unfortunately, such adjustable devices, even with their advantages over the old exoskeletal system, still suffer from aforedescribed drawbacks. In particular, the presently marketed adjustable devices will wear and the adjustments will become loose. Therefore, it becomes necessary for the patient to return to the prosthetist to have his prosthesis tightened and readjusted. With the loosening of the prosthesis, noise may be generated in the various joints which, although not critical to the operation of the device, can become embarassing to the user. In extreme cases, the prosthetic foot has been known to loosen to the point of coming off the prosthetic leg at an inopportune moment.

The development of the endoskeletal prosthesis was a great step forward in artificial limbs and the subsequent adjustability feature has been most helpful in obtaining proper fit. However, the adjustability feature is not needed once a satisfactory fit has been obtained. Fixing or stabilizing the rather expensive adjustable fittings is not economically sound, nor particularly sound from an engineering point of view. To weld the expensive adjustable fittings once a satisfactory fit has been obtained would not only be wasteful, but could add unnecessary weight to the prosthesis. Accordingly, a method has been devised and is disclosed herein to overcome the lasting disadvantages of the adjustable prosthesis while temporarily utilizing the adjustable prosthesis to obtain a satisfactory fit on a patient. Along with the method, particular structural elements have been invented to practice the invention.

SUMMARY OF THE INVENTION

This invention discloses a unique link structure which permits fixture of the various elements one to the other in a permanent fashion, such as by welding or brazing. This link structure includes a domed element and a beveled coupling which may be placed in an abutting relationship with the domed structure for permanent bonding thereto.

BRIEF DESCRIPTION OF THE DRAWINGS

FIG. 1 illustrates an endoskeletal prosthesis shown partly in section, mounted on a transfer device.

FIG. 2 shows the same endoskeletal prosthesis in a front elevation view.

FIG. 3 illustrates a clamp for holding the knee joint in the transfer device illustrated in FIGS. 1 and 2.

FIG. 4 is a side elevation view of a portion of the prosthesis shown in FIGS. 1 and 2, and illustrating the structure of the various elements.

FIG. 5 is a detailed view of an articulated knee joint in accord with the structure disclosed in the present invention.

FIG. 6 is the front elevation view of the same knee joint shown in FIG. 5.

FIG. 7 is a sectional view taken at line 7—7 of the knee joint illustrated in FIG. 5.

FIG. 8 is a perspective view of the base utilized for affixing a prosthetic foot to a prosthetic device.

DETAILED DESCRIPTION OF THE PREFERRED METHOD

The preferred method of performing this invention involves the use of an adjustable prosthetic device (not shown) and uniquely designed elements to make up a prosthetic device which are stabilized in accord with the following steps. The method will be described in the context of the uniquely described elements to be stabilized and in relation to FIGS. 1, 2 and 3.

In a lower limb amputation the method involves fitting a pylon to a prosthetic foot and to the socket in a particular relation unique to the amputee.

The method may also involve, in a lower limb amputation, fitting a pylon to a molded socket, an articulated knee to the pylon, a second pylon to the knee, and prosthetic foot to the second pylon. Such a device is shown ready for stabilization in FIGS. 1 and 2. However, before positioning the aforedescribed elements in the transfer device 10 of FIGS. 1 and 2, which serves as a reference or datum, the orientation of the amputee's prosthesis must first be determined by dynamically fitting a prosthesis to the amputee.

The process of fitting an adjustable prosthesis to an amputee is well known in the art and is not herein illustrated, but will be broadly described as a portion of the method. In every amputation of a lower limb, the amputee undergoes a period of adjustment to the artificial limb. Initially, the artificial limb is dimensioned by the experience of the prosthetist in relation to the remaining limb or to the information obtained before amputation or simply upon the experience of the prosthetist. With reference to the unique elements of FIGS. 1 and 2, such adjustment may require positioning of a torque absorber relative a socket which has been molded to fit the amputee's stump which is illustrated in FIG. 1 as a molded stump 16. Torque absorbers may be necessary for patients wherein trauma to the stump is a factor. The torque absorber allows rotation of the socket and hence the stump relative the prosthetic foot. During walking such rotation is normal so that without a torque absorber either the stump rotates in the socket or the foot rotates while engaged with the walking surface. The length of the prosthesis may be adjusted by appropriate cutting of an upper pylon and a lower pylon. The initial length adjustment is relatively easily determined from the height of the amputee based on his remaining good leg or, in the case of a double amputee, on the build of the individual.

The height adjustment of the upper pylon and lower pylon may, however, be changed as the positioning of the torque absorber, the adjustable knee joint, and the prosthetic foot are adjusted to the patient's needs. Such positioning is accomplished through the use of adjustable prosthetic devices which may include elements such as those disclosed in, for example, U.S. Pat. No. 3,659,294, issued to Richard Glabiszeweski, and other devices well known in the art.

Adjustment of the artificial prosthesis to fit a particular individual may take a period of several months and includes training sessions to insure the amputee is utilizing the prosthesis to its best advantage. Referring specifically to FIGS. 1 and 2, the prosthesis, when it is finally adjusted, may be placed in a transfer device such as transfer device 10.

It is to be understood that the prosthesis shown in FIGS. 1 and 2 is the prosthesis to be stabilized and is not the adjustable prosthesis just described. There are several critical positioning problems in fitting an artificial prosthesis. Initially, the appropriate torque absorber and the upper pylon in an adjustable prosthesis comparable to torque absorber 12 and pylon 18 in FIG. 1 are fitted to the patient based on the experience of the prosthetist. In the plane of the paper, as illustrated in FIG. 1, or the parasaggital plane of the patient, this positioning may be determined in part depending on the patient's age. Placing the comparable torque absorber 12 and pylon 18 in a more posterior position relative socket 14 than illustrated in FIG. 1 may be appropriate for a young, muscular type, while placing the torque absorber and the pylon in a more anterior orientation relative the socket would be appropriate for an elderly patient.

Most critical is the positioning of the articulating knee joint of the adjustable prosthesis comparable to articulating knee joint 22. It should be evident to those skilled in the art that it is a combination of the positioning of the knee joint and the prosthetic foot that determines the balance of the amputee. In FIG. 2 the position of knee joint 22 is an exaggerated "bow-legged" orientation to emphasize the flexibility required in fitting. In general, the center of gravity of the patient should be positioned comfortably over the center of the prosthetic foot. Once comfortable adjustment has been attained by the prosthetist using a temporary adjustable artificial limb, a process which may take several months, the adjustable artificial limb is placed in a datum such as transfer device 10.

The transfer device 10 serves as a jig to establish the orientation and position of each critical element of the adjustable prosthetic device relative the datum so that elements of the "to be stabilized" prosthetic device may be positioned in the device for stabilization. In particular, the stump 16, which has been molded from the patient, is positioned somewhat arbitrarily in an upper bracket 26, which is movable upwardly and downwardly relative the transfer device by means well known in the art. It should be understood the transfer device, such as illustrated here, is also well known in the art. The socket corresponding to socket 14 of the adjustable prosthetic device is then placed over the stump 16 so that the knee and foot subtend therefrom. The lower bracket 28, which has two degrees of freedom, is then positioned in a reference point of the adjustable prosthetic foot which has a counterpart reference point on the devices to be stabilized. This reference point may be a hexagonal socketed screw such as socket head screw 30 which is used in the device to be stabilized. Once the prosthetic foot of the adjustable prosthetic device is fixed in lower bracket 28, the central bracket 32 (see FIG. 3), which includes a bifurcated element 34, may be positioned about the axis of the knee joint of the adjustable prosthesis. It should be understood that central bracket 32 is movable vertically and laterally and also rotates. Bifurcated element 34 includes a fixed leg 35 and an adjustable leg 36, which is movable inwardly and outwardly of a reference point specifically the axis of rotation of the articulated knee joint, so that the position and axis of rotation of the knee joint may be determined relative the datum. It can be seen, at this point, that having positioned the adjustable artificial limb in the transfer device 10, the position of the prosthetic foot relative the datum has been established. Furthermore, the position of the articulated knee joint has also been established relative the prosthetic foot of the adjustable prosthetic device and also relative the socket of the adjustable prosthetic device.

Once these positions have been established as indicated above, the adjustable prosthetic device is removed from the transfer device 10 by relieving bifurcated leg 36 without disturbing the relationship of the bifurcated element 34 relative the datum. Secondly, the upper bracket 26 and the lower bracket 28 may be moved away from the central bracket 32 after a stop member 38 for the upper bracket and a stop member 40 for the lower bracket 28 are positioned against the brackets. Upper bracket 26 and lower bracket 28 may be prevented from rotation about the vertical member 42 of transfer device 10 by a slot or groove 44 which runs longitudinally in the upright member 42 and in which a tongue of the upper and lower brackets will travel.

Once the adjustable limb is removed from the transfer device, the transfer device then becomes a jig to build up the elements of the "to be stabilized" prosthesis. Initially, the knee joint 22, which may be fitted with a torque absorber 12 is positioned in the central bracket 32. (Reference should be made to FIG. 6, wherein a knee joint appropriate for use in this method is shown in detail.) It will be noted that knee joint 22 shown in FIG. 6 has indentation 46 and 48 in either end of the axis of rotation of the knee joint formed by a bolt member 50 (see FIG. 7). With knee joint 22 in position in central bracket 32, upper pylon 18 which may be of rigid plastic foam may be positioned relative the stump mold 16, knee joint 22 and the affixed torque absorber 12, which itself is the subject of application Ser. No. 805,059, now U.S. Pat. No. 4,134,159. Upper pylon 18 may be affixed to flange 56 of torque absorber 12 (or to a similar flange integrally formed with knee joint 22 when a torque absorber is contra-indicated) by an epoxy adhesive or the like.

Socket 14, after lowering of the bracket 26 and stump mold 16 to the previously determined position, may be then molded about torque absorber 12, upper pylon 18 and stump mold 16 in a manner well known in the art using a medium such as glass fibers and bonding agents or the like. It has been found helpful to use a partial vacuum in introducing a bonding agent to a flexible mold in forming socket 14.

Lower pylon 20 may then be placed in position between knee 22 and the prosthetic foot 24 which is fitted with a base 58 (see FIG. 8). Placed at either end of pylon 20 are couplings 52 at the upper end and 52' at the lower end. Couplings 52 and 52' may be identical, and each will have a beveled surface 54 (see FIGS. 5 and 8). The beveled surface 54 of coupling 52 may be placed in an abutting relationship with a domed surface 60 on the lower portion of knee joint 22. Similarly, the beveled surface 54 of coupling 52' may be placed in an abutting relationship with a domed surface 62 formed on base 58. It is to be understood that lower bracket 28 is returned to the determined position found in the earlier step from the adjustable leg.

In one type of structure envisioned for use in this method of fitting a stabilized artificial prosthesis, certain inflammable elements should be removed from the knee joint and the foot prior to bonding of the surface together. For example, the resilient member 64, located in knee joint 22, should be removed and replaced with a non-flammable spacer during the bonding process. Similarly, the prosthetic foot 24 may also have to be removed, depending upon the flammability of the foot. It should be noted that socket head screw 30 may be extended to its normal position once the prosthetic foot 24 is removed from the transfer device 10, which is the datum. With the flammable members removed from knee joint 22 and from prosthetic foot 24, the beveled surfaces 54 may be bonded to the domed surfaces 60 and 62 respectively by welding, brazing, or the like.

Once the bonding process is complete, the various flammable members removed before bonding may be replaced, and construction of the cosmetic surfaces of the artificial leg denoted by the dashed lines 66 in FIG. 4 may be constructed in a manner well known in the art.

Although subsequent adjustment has not proved necessary in use of this particular device, adjustment could be accomplished by removal of the cosmetic surface 60.

It will be understood by those skilled in the art that a below-the-knee prosthesis stabilization would follow from the above description by eliminating the knee joint. In such a prosthesis the torque absorber 12 if used would be fitted with a clamp similar to coupling 52 for fixture to pylon 20. The fitting of the foot would follow using the structure shown in FIG. 8. The torque absorber would then be molded to the stump mold 16.

THE UNIQUE STRUCTURE

Although it should be apparent to those in the art what the particulars of the unique structure herein disclosed are at this point following the discussion of the method, a detailed description of the structure follows.

In particular, this invention envisions a domed surface formed on one element which may replace a joint such as a knee or ankle as shown in FIGS. 5 and 8 and used in conjunction with the beveled surface formed on a second element such as beveled surface 54 found on representative coupling 52 the two forming a link for interconnecting two parts of a prosthesis.

Referring specifically to FIGS. 5 and 6, it will be seen that articulating knee joint 22 is formed with a first portion 70 which may be adapted to have permanently affixed thereto a torque absorber 12 and a second portion 72 fixable to the lower pylon 20 by coupling 52. It should be understood that upper portion 70 may be affixed directly to pylon 18 by means such as epoxy type adhesive if a torque absorber 12 is contra-indicated. In this case the knee joint 22 would be formed with an integrally formed flange in the manner of flange 56 of torque absorber 12 so that socket 14 could be formed thereabout. A simple expedient in manufacturing is to form all knee joints 22 with a flange which may be removed to allow bonding of the torque absorber. First portion 70 has subtending a bifurcated structure 74 through which axle 50 of the articulated joint passes. Similarly, the second portion 72 is bored as at 76 to receive bushing means such as bushing 78 which may be of a plastic polymer material well known in the art and which serves as a permanent bearing. Affixed to second portion 72 is the resilient member 64 by a bolt 65 or the like. Resilient member 64 is disposed between the first portion 70 and the second portion 72 to form the mating surface with the first portion 70. Resilient member 64 may be of an elastomer or the like to provide means for absorbing a certain degree of shock as the articulation closes. It will be understood by those familiar with the art that as the artificial limb is used, the motion of the amputee in swinging the artificial leg forward will close the articulated joint so that resilient member 64 will come in contact with the first portion 70 in the manner of a locking knee.

One of the important features of the knee joint 22 is the domed surface 60, to which a representative coupling 52 may be affixed. Coupling 52 is generally a hollow cylinder and is formed with a hollow frustoconical end thereby defining a beveled surface 54 to form an appropriate joint with the domed surface of the mating element to which the coupling 52 may be welded or brazed. At the other end of coupling 52, a tangential boss 80 may be formed having a bore 82 therethrough (see FIG. 6) in which an adjusting bolt 84 may be threadably engaged. An axially aligned slot 86 may be formed through the boss 80 and a coupling 52 so that tightening of bolt 84 which may be socket headed, causes the coupling 52 to act as a clamp on the tubular pylon 20, thus fixing the coupling 52 to the pylon 20 to form skeletal pylon means to interconnect a knee with a foot. It should be noted that only one portion of the bore 82 formed in boss 80 may be threaded, with the other portion being of a diameter sufficient to receive bolt 84 without engagement of the threads.

Referring to FIG. 8, it can be seen that the base 58 is formed, in the manner previously described for a knee 22, with a domed head 62. In particular, base 58 is an elongated plate member with the dome 62 extending outwardly from one side thereof. A threaded bore 90 is formed in the center of dome 62 to threadably receive screw 30 which may have a socket head. A washer 92 may be disposed between the head of screw 30 and the prosthetic foot 24 molded to fit on base 58.

Operation of the structure herein described should be evident from the method previously described; however, in review, the beveled surface 54 of a representative coupling is placed in an abutting relationship with a domed surface of the knee joint or the base plate as appropriate and in the angular relationship determined by the dynamic alignment of the adjustable prosthetic device. Once the beveled end is in this relationship and held there with the transfer device 10 forming a datum, the beveled end 54 is bonded with the domed surface by welding, brazing, or the like.

The combination of the dome and bevel as described herein allows the elements of the prosthesis to be positioned in various angular orientations while retaining the V-joint appropriate for proper metallic bonding.

Although this invention has been described in relation to a particular method and a unique structure, it is to be understood that variations within the skill of the art are to be considered within the purview of this description.

The embodiments of the invention in which an exclusive property or privilege is claimed are defined as follows:

1. A link for interconnecting two parts of a prosthetic limb comprising:
   a domed element and a hollow cylindrical coupling defining a beveled outer surface at one end thereof;
   said hollow cylindrical coupling positionable with said beveled outer surface adjacent said domed element to form a bondable joint therebetween.

2. The link set forth in claim 1 wherein the domed element comprises a prosthetic articulated knee, including a first portion and a second portion joined together by hinge means for para-saggital motion in an artificial leg, said second portion having a domed extension.

3. A link set forth in claim 2 wherein the hollow cylindrical coupling defines a slot extending axially from the other second end to a point proximate the beveled surface and further defines a tangential transverse boss split by said slot into a first part and a second part, said first and second parts bored with said bore of said second part threaded;
   a bolt threadably engageable in said second part so that with said bolt extending through said bore in said first part to engage said bore in said second part, said bolt may be rotated to cause said slot to close whereby said coupling acts as a clamp.

4. The link set forth in claim 1 wherein the domed element comprises a base unit adapted to receive a prosthetic foot and having a domed extension on one surface.

5. The link set forth in claim 4 wherein the hollow cylindrical coupling defines a slot extending axially from the other second end to a point proximate the beveled surface and further defines a tangential transverse boss split by said slot into a first part and a second part, said first and second parts bored with said bore of said second part threaded;
   a bolt threadably engageable in said second part so that with said bolt extending through said bore in said first part to engage said bore in said second part, said bolt may be rotated to cause said slot to close whereby said coupling acts as a clamp.

6. A joint replacement assembly and a pylon coupling for a lower limb prosthesis comprising:
   a domed element integrally formed with said joint replacement assembly; and
   a hollow fusto-conical element integrally formed with said pylon coupling and positionable in an abutting relation with said domed element for permanent bonding thereto.

7. The invention of claim 6 wherein the joint replacement assembly comprises:
   a first member;
   a second member;
   hinge means interconnecting said first and said second members for articulation of said first and said second members relative each other;
   said second member defining the domed surface for interconnection by permanent bonding with the pylon coupling.

8. The invention of claim 7 further comprising means for absorbing shock resulting from articulation of the first and second members.

9. The invention of claim 8 wherein the first member defines a subtending bifurcated portion and further wherein the second portion defines a bore, said subtending bifurcated portion bored and alignable with the bored second portion to receive the hinge means.

10. The invention of claim 9 wherein the hinge means comprises:
    a hinge pin adapted to be received in the bored first and second portions; and
    bearing means disposed in said bored second portion for reducing friction during articulation.

11. The invention of claim 6 wherein the joint replacement assembly comprises:
    base means for receiving a prosthetic foot, said base means having integrally formed therewith the domed element.

* * * * *